United States Patent [19]

Adelstein

[11] 4,017,491
[45] Apr. 12, 1977

[54] 1,1-DIARYL-1H-TETRAZOLE AMINES

[75] Inventor: Gilbert W. Adelstein, Evanston, Ill.

[73] Assignee: G. D. Searle & Co., Chicago, Ill.

[22] Filed: July 28, 1975

[21] Appl. No.: 599,413

Related U.S. Application Data

[63] Continuation-in-part of Ser. No. 456,755, April 1, 1974, Pat. No. 3,917,615, and Ser. No. 568,694, April 16, 1975.

[52] U.S. Cl. ............... 260/247.5 E; 260/293.54; 260/293.69; 260/296 R; 260/308 D; 260/301 G; 260/293.67; 424/272; 424/267; 424/248.4; 424/263

[51] Int. Cl.² ............. C07D 401/06; C07D 403/08

[58] Field of Search ......... 260/247.5 E, 293.54, 260/293.69, 296 R, 308 D

[56] References Cited

UNITED STATES PATENTS

| | | | |
|---|---|---|---|
| 2,604,473 | 7/1952 | Sperber et al. | 260/296 R |
| 2,656,358 | 10/1953 | Sperber et al. | 260/296 R |
| 3,318,869 | 5/1967 | Cusic et al. | 260/293.54 |

OTHER PUBLICATIONS

Adelstein, "J. Med. Chem.," vol. 16, No. 4, pp. 309-312, Apr. 1973.

*Primary Examiner*—Henry R. Jiles
*Assistant Examiner*—Robert T. Bond
*Attorney, Agent, or Firm*—John J. McDonnell

[57] ABSTRACT

The present invention relates to compounds of the following formula

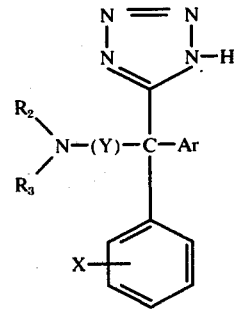

wherein Y is straight or branched chain alkylene containing 1-4 carbon atoms; X is hydrogen, halo such as fluoro, chloro, bromo or iodo, or lower alkyl containing 1-7 carbon atoms; Ar is phenyl, pyridyl, mono-substituted phenyl, wherein the substituent is halo such as fluoro, chloro, or bromo, or lower alkyl having 1-7 carbon atoms; and $R_2$ and $R_3$ are lower alkyl having 1-7 carbon atoms, or $R_2$ and $R_3$ together with N is an azamonocyclic ring selected from the group comprising 1-pyrrolidinyl, piperidino, 4-phenyl-4-hydroxypiperidino, 4-phenyl-4-hydroxymethylene, 4-phenyl-4-carboxypiperidino, 4-phenyl-4-carbloweralkoxypiperidino, or 4-phenyl-4-acetoxypiperidino substituted piperidino and morpholino, or an azabicycloalkanyl containing 6 to 9 carbon atoms and having at least 5 atoms in each ring of the azabicycloalkane. These compounds are useful intermediates for preparing potent antidiarrheal compounds.

16 Claims, No Drawings

1,1-DIARYL-1H-TETRAZOLE AMINES

This is a continuation-in-part of my copending application Ser. No. 456,755 filed Apr. 1, 1974, now U.S. Pat. No. 3,917,615, and Ser. No. 568,694 filed Apr. 16, 1975.

The present invention relates to compounds of the following formula

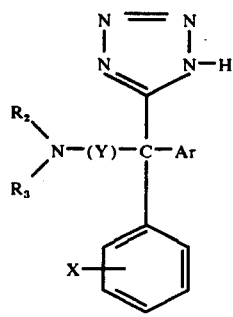

wherein Y is straight or branched chain alkylene containing 1–4 carbon atoms; X is hydrogen, halo such as fluoro, chloro, bromo, iodo, or lower alkyl containing 1–7 carbon atoms; Ar is phenyl, pyridyl, mono-substituted phenyl, wherein the substituent is halo such as fluoro, chloro, bromo or iodo, or lower alkyl having 1–7 carbon atoms; and $R_2$ and $R_3$ are lower alkyl having 1–7 carbon atoms, or $R_2$ and $R_3$ together with N is an azamonocyclic ring selected from the group comprising 1-pyrrolidinyl, piperidino, 4-phenyl-4-hydroxypiperidino, 4-phenyl-4-hydroxymethylpiperidino, 4-phenyl-4-carboxypiperidino, 4-phenyl-4-carbalkoxypiperidino or 4-phenyl-4-acetoxypiperidino substituted piperidino and morpholino, or an azabicycloalkane containing 6 to 9 carbon atoms and having at least 5 atoms in each ring of the azabicycloalkanyl. Thus, $R_2$ and $R_3$ together with N is a heterocyclic ring system comprising monocyclic rings of the formula

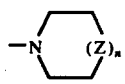

wherein n is 0, 1 and Z is oxygen, methylene, phenyl hydroxymethylene, phenylcarboxymethylene, phenylhydroxymethylmethylene, phenylcarbalkoxymethylene and bicycloazacycloalkane containing 6 to 9 carbon atoms and containing at least 5 atoms in each ring of the azabicycloalkanyl.

The organic bases of this invention form non-toxic, acid-addition salts with a variety of organic and inorganic acids. Such salts are formed with acids such as sulfuric, phosphoric, hydrochloric, hydrobromic, hydriodic, sulfamic, citric, lactic, maleic, malic, succinic, tartaric, cinnamic, acetic, benzoic, fluconic, ascorbic, and related acids.

Compounds of the present invention are prepared as set out in Scheme A

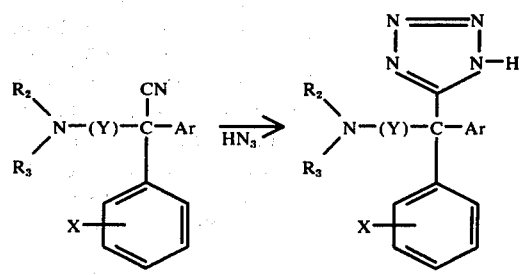

Scheme A wherein $R_1$, $R_2$, $R_3$, Ar, Y, X are as defined above. Methods for preparing nitrile precursors are described in U.S. Pat. No. 3,299,044 and include the reaction of an appropriate amine with a halide of the formula

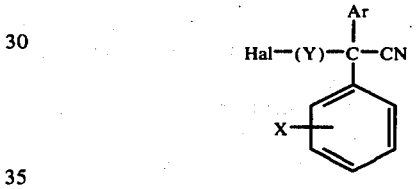

wherein Y, Ar, X are as above and Hal is chlorine or bromine. Alternately, the nitriles can be prepared by the reaction of a diarylacetonitrile of the formula

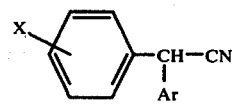

first with sodamide and then with an alkyl halide of the formula

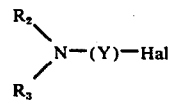

wherein $R_2$, $R_3$, X, Y, Ar, and Hal are as previously described.

1,1-Phenyl substituted amino substituted alkyl nitriles suitable for practicing this invention are described in U.S. Pat. Nos. 3,497,519, 2,841,589, 3,299,044, 2,823,233, 3,225,054 and 3,318,869 and an article by R. Moffett and B. Aspergran, *J. Amer. Chem. Soc.*, 79, 4451 (1957). As shown in Scheme A, treatment of the nitrile with azide ion by methods similar to those described by G. Moersch and D. Morrow, *J. Med. Chem.*, 10, 149 (1967) provides the corresponding tetrazole.

Preferred embodiments of the present invention as set out in formula I in which $R_2$ and $R_3$ together with N is an azamonocyclic ring selected from the group comprising 1-pyrrolidinyl, piperidino, 4-phenyl-4-carboxypiperidino, 4-phenyl-4-hydroxymethyl, 4-phenyl-4-carbalkoxypiperidino, 4-phenyl-4-hydroxypiperidino or acetoxy substituted piperidino, and morpholino are those in which Y is ethylene, propylene, or isopropylene; Ar is phenyl or 2-pyridyl; and X is hydrogen. Specifically these compounds are useful in preparing 5-{[1,1-diphenyl-3-(4-hydroxy-4-phenyl)piperidino]propyl}-2-methyl-1,3,4-oxadiazole, 5-{[1,1-diphenyl-3-(4-acetoxy-4-phenyl)piperidino]propyl}-2-methyl-1,3,4-oxadiazole, 5-[(1,1-diphenyl-3-piperidino)propyl]-2-methyl-1,3,4-oxadiazole, 5-[(1,1-diphenyl-3-morpholino)propyl]-2-methyl-1,3,4-oxadiazole, 5-[(1,1-diphenyl-3-pyrrolidinyl)propyl]-2-methyl-1,3,4-oxadiazole, 5-{[1,1-diphenyl-3-(4-carboxy-4-phenyl)piperidino]propyl}-2-methyl-1,3,4-oxadiazole and the basic salts thereof such as sodium or potassium salts of the acid 4-{[1,1-diphenyl-3-(4-carboxy-4-phenyl)piperidino]propyl}-2-methyl-1,3,4-oxadiazole.

Preferred embodiments of the present invention as set out in formula I in which $R_2$ and $R_3$ together with N is an azabicycloalkyl structure containing 6–9 carbon atoms and containing at least 5 atoms in each ring of the azabicycloalkyl structure are those wherein Y is ethylene, propylene, isopropylene; Ar is phenyl or pyridyl; and X is hydrogen. Specifically these compounds are useful in preparing 5-{[1,1-diphenyl-3-(2-azabicyclo[2·2·2]oct-2-yl)]propyl}-2-methyl-1,3,4-oxadiazole, 5-[1,1-diphenyl-3-(2-azabicyclo[2·2·2]oct-2-yl)propyl]-2-ethyl-1,3,4-oxadiazole, 5-{[1,1-diphenyl-3-(3-azabicyclo[3·2·2]non-3-yl)]propyl}-2-methyl-1,3,4-oxadiazole, 5-{[1-phenyl-1-(2-pyridyl)-3-(3-azabicyclo[3·2·2]non-3-yl)]propyl}-2-methyl-1,3,4-oxodiazole, 5-{[1,1-diphenyl-3-(4-azabiclo[2·2·1]hept-7-yl)]propyl}-2-methyl-1,3,4-oxadiazole, 5-{[1,1-diphenyl-3-(6-azabicyclo[3·2·1]oct-6-yl)]propyl}-2-methyl-1,3,4-oxadiazole, 5-{[1-(4-chlorophenyl)-1-(4-methylphenyl)-3-(2-azabicyclo[2·2·2]oct-2-yl)]butyl}-2-methyl-1,3,4-oxadiazole and 5-{[1,1-diphenyl-3-(8-azabicyclo[4·3·0]non-8-yl)]propyl}-2-methyl-1,3,4-oxadiazole.

Compounds of the present invention are converted into useful antidiarrheal and antiarrhythmic compounds by the reaction sequence set out in Scheme B

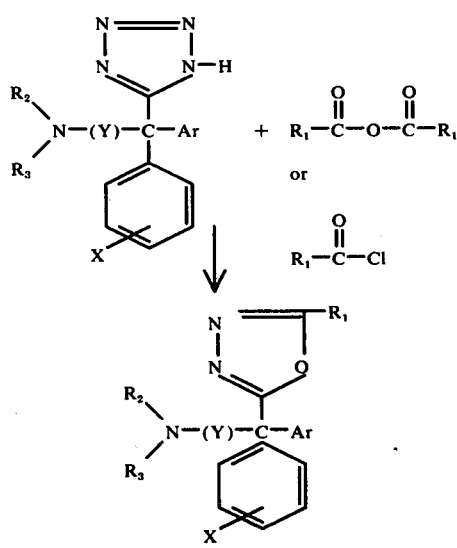

wherein $R_2$, $R_3$, Y, Ar, and X are as previously defined and $R_1$ is lower alkyl having 1–7 carbon atoms, trifluoromethyl, adamantyl, phenyl, or X substituted phenyl — X having the earlier set out definition The conversion set out in Scheme C wherein Ar is phenyl or pyridyl and $R_1$ is lower alkyl having 1–7 carbon atoms, phenyl, trifluoromethyl, 1-adamantyl(tricyclo[3·3·1·1$^{3,7}$]decyl.

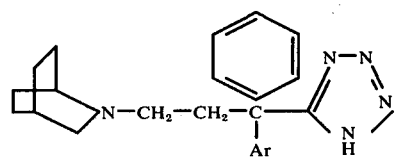

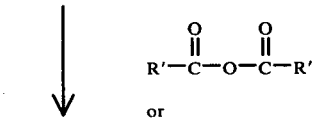

or

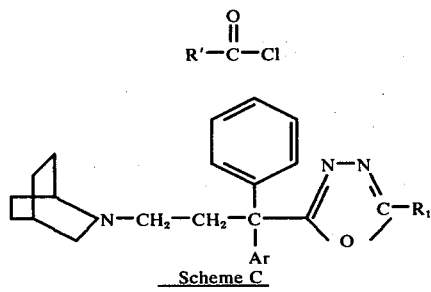

Scheme C is preferred. Thus, 5-[1,1-diphenyl-3-(2-azabicyclo[2·2·2]oct-2-yl)]propyl-1H-tetrazole is an intermediate in preparing the following anti-diarrheal agents: 5-{[1,1-diphenyl-3-(2-azabicyclo[2·2·2]oct-2-yl)]propyl}-2-methyl-1,3,4-oxadiazole; 5-{[1,1-diphenyl-3-(2-azabicyclo[2·2·2]oct-2-yl)]propyl}-2-trifluoromethyl-1,3,4-oxadiazole; 5-{[1,1-diphenyl-3-(2-azabicyclo[2·2·2]oct-2-yl)]propyl}-2-phenyl-1,3,4-oxadiazole; 5-{[1,1-diphenyl-3-(2-azabicyclo[2·2·2]oct-2-yl)propyl}-2-(1-tricyclo[3·3·1·1$^{3,7}$]decyl)-1,3,4-oxadiazole; 5-{[1-phenyl-1-(3-pyridyl)-3-(2-azabicyclo[2·2·2]oct-2-yl)]propyl}-2-methyl-1,3,4-oxadiazole.

As shown in Scheme B the tetrazole intermediates are converted to the corresponding 1,3,4-oxadiazole by treatment with an acid anhydride or acid chloride following the procedures substantially as described by R. Huisgen et al., Chem. Ber., 93, 2106 (1960).

For instance, 26.3 parts of 2,2-di-phenyl-4-(2-azabicyclo[2·2·2]oct-2-yl)butyronitrile described in U.S. Pat. No. 3,318,869 is dissolved in 60 parts by volume of dimethylformamide along with 9.0 parts of sodium azide, 7.4 parts of ammonium chloride and 0.12 parts of lithium chloride and refluxed for 12 hours. Upon reflux a solid separates which is 5-[1,1-diphenyl-3-(2-azabicyclo[2·2·2]oct-2-yl)]propyl)-1H-tetrazole. 11.2 Parts of this tetrazole intermediate and 13.04 parts of acetic anhydride are dissolved in 50 parts by volume of pyridine and refluxed for 2 hours. The solution is cooled and the solid filtered. The filtrate is evaporated to dryness and the residue is slurried in potassium carbonate solution, extracted with methylene chloride, and the methylene chloride extracts are washed with water and dried. Crystallization provides 5-{[1,1-diphenyl-3-(2-aaabicyclo[2·2·2]oct-2-yl)]propyl}-2-ethyl-1,3,4-oxadiazole melting at 100°–102° C.

Anti-diarrheal utility of the oxadiazole compounds for which the present compounds are intermediates is evidenced by the former's ability to inhibit gastrointestinal mobility as set out in the following test.

CHARCOAL MEAL TEST

Mice weighing 18–24 grams and previously fasted for 18 hours were each given orally 0.3 ml. of a suspension containing 10% charcoal and 5% acacia. The test compounds were administered intragastrically one hour prior to the charcoal meal. One-half hour after administration of the meal the mice were sacrificed with ether and their gastrointestinal tracts were removed. The distance over which some of the charcoal meal had moved from the pylorus to the cecum was measured for each mouse and expressed as percentage of the total distance. Each compound was tested at three dose levels (typically, at 0.3, 0.6 and 1.2 mg./mouse) in groups of 5 mice per dose level. Control groups of mice given saline only were run concurrently with each test group.

The anti-arrhythmic utility of the oxadiazoles for which the present compounds are an intermediate is evident from the results of a standardized test for their capacity to slow the ventricular tachycardia induced by aconitine in the isolated rabbit heart. The procedure is essentially that described by Lucchesi, *J. Pharmacol. Exp. Therap.*, 137, 291 (1962), modified in certain particulars as follows: Hearts are obtained from adult albino rabbits of either sex and perfused in apparatus modeled after that devised by Anderson and Craver, *J. Pharmacol. Exp. Therap.*, 93, 135 (1948). Composition of the perfusion solution is the same as Lucchesi's, but the volume is increased to 200 ml. and the temperature lowered to 28° C. Aconitine (ordinarily as the nitrate) is administered as soon as the heart beat is regular and the EKG pattern normal, the dose being so selected as to at least double the rate. Typically, 0.05 ml. of 0.1% aconitine nitrate in physiological saline is injected. EKG's are recorded at five minute intervals after onset of ventricular tachycardia until two successive readings show stabilization of the rate. Perfusate collected during this time is discarded and replaced with fresh solution q.s. 200 ml. Promptly following stabilization, 2 mg. of compound dissolved or suspended in 1 ml. of physiological saline, is mixed with the perfusion solution. Ten minutes later a like amount is introduced, followed after a further ten minutes by double the first amount. Final concentration of compound in the perfusion solution is thus 40 mg. per l. Recording of EKG's is continued at five minute intervals throughout this time and for ten minutes thereafter. A compound is considered anti-arrhythmic if, at any time during the 30 minutes immediately following initial administration in at least half of a minimum of two tests, it reduces by 50% or more the rate recorded ten minutes after onset of tachycardia.

The following examples are presented to further illustrate the present invention. They should not be construed as limiting it either in scope or in spirit. In these examples quantities are indicated in parts by weight unless parts by volume are specified, and temperatures are indicated in degrees Centigrade (°C.).

EXAMPLE 1

26.3 Parts of 2,2-diphenyl-4-(2-azabicyclo[2·2·2]oct-2-yl)butyronitrile described in U.S. Pat. No. 3,318,869 is dissolved in 60 parts by volume of dimethylformamide along with 9.0 parts of sodium azide. 7.4 Parts of ammonium chloride and 0.12 parts of lithium chloride and refluxed for 12 hours. Upon reflux a solid separates which is 5-[1,1-diphenyl-3-(2-azabicyclo[2·2·2]oct-2-yl)]propyl-1H-tetrazole m.p. 303° (dec). 11.2 Parts of this tetrazole intermediate and 13.04 parts of acetic anhydride are dissolved in 50 parts by volume of pyridine and refluxed for 2 hours. The solution is cooled. The filtrate is evaporated to dryness and the residue is slurried in potassium carbonate solution, extracted with methylene chloride, and the methylene chloride extracts are washed with water and dried. Crystallization provides 5-{[1,1-diphenyl-3-(2-azabicyclo[2·2·2]oct-2-yl)]propyl}-2-methyl-1,3,4-oxadiazole, melting at 100°–102° C. The structure of the tetrazole intermediate is:

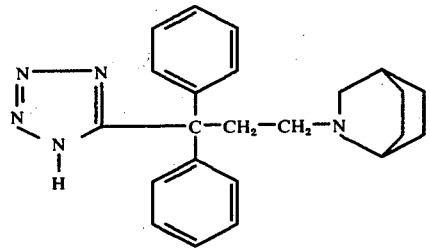

EXAMPLE 2

36 Parts of 2,2-diphenyl-4-(3-azabicyclo[3·2·2]non-3-yl)butyronitrile (U.S. Pat. No. 3,318,864), 9.8 parts of sodium azide, 8.06 parts of ammonium chloride, and 0.15 part of lithium chloride are placed in 50 parts by volume of dimethylformamide and heated at 125° C for 12 hours. The solution is cooled and a white solid is filtered off. The solid is washed with dimethylformamide and water and then dried. This procedure provides 5-[1,1-diphenyl-3-(3-azabicyclo[3·2·2]non-3-yl)]propyl-1H-tetrazole melting at 284°–286° C.

10.0 Parts of this 1H-tetrazole and 20.5 parts of acetic anhydride are refluxed for 1 hour in 100 parts by volume of pyridine. The solution is cooled and the pyridine is removed by evaporation at reduced pressure. The residue is taken up in ether and the ether solution is then washed with dilute sodium bicarbonate. The ether is then removed by evaporation at reduced pressure and the residual solid is recrystallized from ether-n-pentane and dried in vacuo to provide 5-{[1,1-diphenyl-3-(3-azabicyclo[3·2·2]non-3-yl)]propyl}-2-methyl-1,3,4-oxadiazole, melting at 137°–140° C. The tetrazole intermediate has the following formula

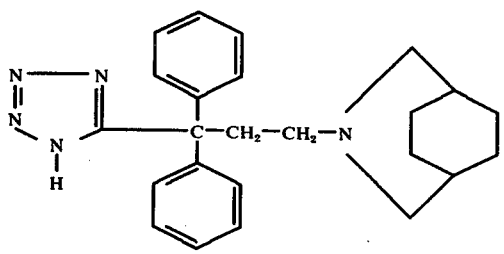

EXAMPLE 3

Using equivalent amounts and following the procedure set out in Example 2, 2-phenyl-2-(2-pyridyl)-4-(3-azabicyclo[3·2·2]non-3-yl)butyronitrile described in U.S. Pat. No. 3,318,869 is converted to 5-[1-phenyl-1-(2-pyridyl)-3-(3-azabicyclo[3·2·2]non-3-yl)]propyl-1H-tetrazole, melting at 245–246° C, and this tetrazole is then converted to 5-{[1-phenyl-1-(2-pyridyl)-3-(3-azabicyclo[3·2·2]non-3-yl)]propyl}-2-methyl-1,3,4-oxadiazole, melting at 117.5°–120° C. The tetrazole intermediate has the following formula

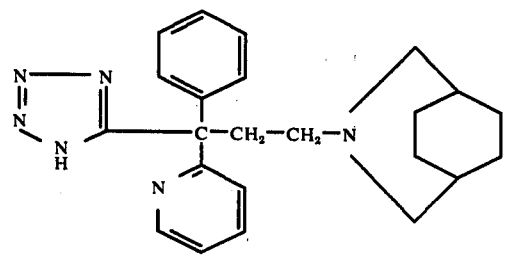

EXAMPLE 4

Using equivalent amounts and following the procedure set out in Example 2, 2-phenyl-2-(2-pyridyl)-4-(3-azabicyclo[3·2·2]non-3-yl)valeronitrile described in U.S. Pat. No. 3,318,869 is converted to 5-[1-phenyl-1-(2-pyridyl)-4-(3-azabicyclo[3·2·2]non-3-yl)]butyl-1H-tetrazole which in turn is converted to 5- [1-phenyl-1-(2-pyridyl)-4-(3-azabicyclo[3·2·2]non-3-yl)]butyl -2-methyl-1,3,4-oxadiazole. The tetrazole intermediate has the following formula

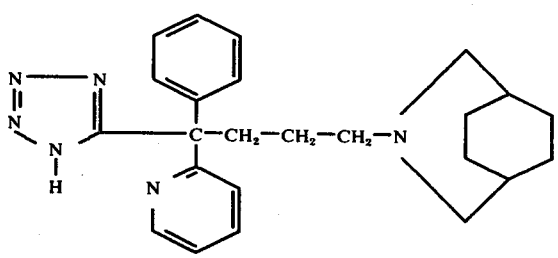

EXAMPLE 5

Using equivalent amounts and following the procedure in Example 2, 2,2-diphenyl-4-(8-azabicyclo[4·3·0]non-8-yl)butyronitrile, described in U.S. Pat. No. 3,318,869, is converted to 5-[1,1-diphenyl-3-(8-azabicyclo[4·3·0]non-8-yl)]propyl-1H-tetrazole which is then converted to 5-{[1,1-diphenyl-3-(8-azabicyclo[4·3·0]non-8-yl)]propyl}-2-methyl-1,3,4-oxadiazole. The tetrazole intermediate has the following formula

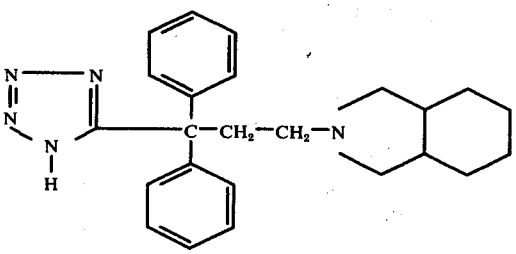

EXAMPLE 6

Using equivalent amounts and following the procedure in Example 2, 2,2-diphenyl-4-(6-azabicyclo[3·2·1]oct-6-yl)butyronitrile described in U.S. Pat. No. 3,318,869 is converted to 5-[1,1-diphenyl-3-(6-azabicyclo[3·2·1]oct-6-yl)]propyl-1H-tetrazole which is then converted to 5-{[1,1-diphenyl-3-(6-azabicyclo[3·2·1]oct-6-yl)]propyl}-2-methyl-1,3,4-oxadiazole. The tetrazole intermediate has the following formula

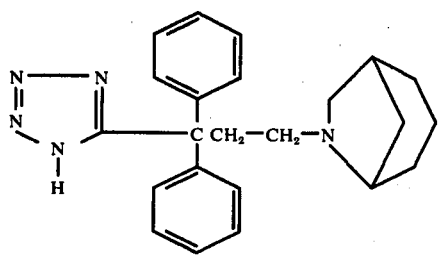

EXAMPLE 7

15 Parts of 2,2-diphenyl-4-bromobutyronitrile are condensed with 12.9 parts of 7-azabicyclo[2·2·1]heptane by reflux in 100 parts by volume of ethylene glycol monomethyl ether. The reaction mixture is cooled and extracted with dilute hydrochloric acid. The aqueous hydrochloric acid extract is made basic with sodium hydroxide solution and extracted with ether. The ether extracts are dried over anhydrous sodium sulfate. Filtration and removal of the ether by evaporation at reduced pressure provides 2,2-diphenyl-4-(4-azabicyclo[2·2·1]hept-7-yl)butyronitrile, melting at 79°–81° C. 4.9 Parts of this butyronitrile, 1.5 parts of sodium azide, 1.2 parts of ammonium chloride, and 0.023 parts of lithium chloride are placed in 50 parts by volume of dimethylformamide and heated at 125° C for 12 hours. The mixture is cooled and the solid is filtered from the dimethylformamide. The solid is washed with dimethylformamide and water. The dried solid is 5-[1,1-diphenyl-3-(7-azabicyclo[2·2·1]hept-7-yl)]propyl-1H-tetrazole, melting at 284°–286° C.

2.15 Parts of the above tetrazole and 4.9 parts of acetic anhydride are refluxed in 20 parts by volume of pyridine for 1 hour. The reaction mixture is cooled. The pyridine is removed by evaporation at reduced pressure to provide a residue. The residue is taken up in ether. The ether is washed with sodium bicarbonate solution. The ether is then removed to provide a crude product which upon recrystallization from pentane provides 5-{[1,1-diphenyl-3-(7-azabicyclo[2.2.1]hept-7-yl)]propyl}-2-methyl-1,3,4-oxadiazole, melting at 130–132° C. The tetrazole intermediate has the following formula

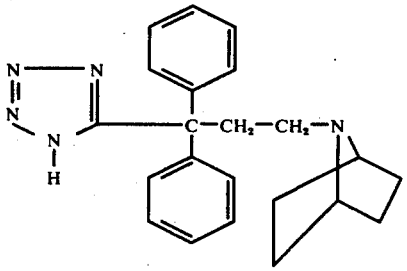

EXAMPLE 8

15 Parts of 2,2-diphenyl-4-bromobutyronitrile, 8.9 parts of 4-hydroxy-4-phenylpiperidine and 400 parts by volume of ethylene glycol monomethyl ether are heated together at reflux for 18 hours under nitrogen. The solution is cooled and the volume is reduced 50% at 60° C under reduced pressure. The concentrated mixture is diluted with 1200 parts of water, made basic with sodium hydroxide, and then extracted with ether. The product is isolated from ether by extraction into acid solution followed by making the solution basic and extracting with ether. The dried product is 2,2-diphenyl-4-(4-hydroxy-4-phenyl)piperidinobutyronitrile, melting at 221°–223° C.

8.0 Parts of this nitrile, 2.0 parts of sodium azide, 1.6 parts ammonium chloride, 0.030 parts of lithium chloride and 20 parts by volume of dimethylformamide are by the method of Example 7 converted to 5-[1,1-diphenyl-3-(4-hydroxy-4-phenylpiperidino)]propyl-1H-tetrazole. Also as described in Example 7, 316 parts of the above 1H-tetrazole, 7.1 parts acetic anhydride, and 36 parts by volume of pyridine are converted to 5-{[1,1-diphenyl-3-(4-acetoxy-4-phenyl)piperidino]propyl}-2-methyl-1,3,4-oxadiazole, melting at 157.5°–160° C. The tetrazole intermediate has the following formula

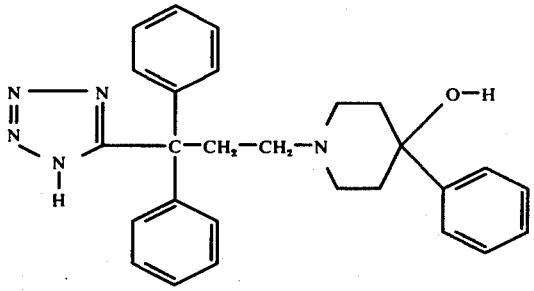

EXAMPLE 9

Using equivalent parts and following the procedure set out in Example 8, 2,2-diphenyl-4-(4-carbethoxy-4-phenyl)piperidinebutyronitrile described in U.S. Pat. No. 3,497,519 is converted to 5-[1,1-diphenyl-3-(4-carbethoxy-4-phenylpiperidino)]propyl-1H-tetrazole. Also according to Example 8, and using equivalent parts, the 1H-tetrazole is converted to 5-{[1,1-diphenyl-3-(4-carbethoxy-4-phenyl)piperidino]propyl}-2-methyl-1,3,4-oxadiazole. The tetrazole intermediate has the following formula

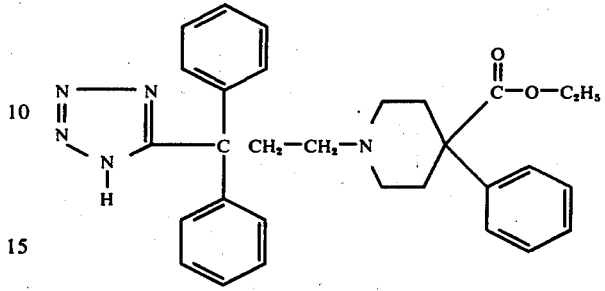

EXAMPLE 10

Following the procedures set out in Example 1, 36.5 parts of 2,2-diphenyl-4-diisopropylaminobutyronitrile (U.S. Pat. No. 2,823,233), 7.95 parts of ammonium chloride, 9.75 parts sodium azide, and 0.15 part of lithium chloride in 75 parts by volume of dimethylformamide are converted to 5-[1,1-diphenyl-3-(diisopropylamino)]propyl-1H-tetrazole, melting at 272°–274° C. Also following the procedures set out in Example 1, 1.2 parts of the 1H-tetrazole is reacted with 1.1 parts of acetyl chloride in 10 parts by volume of pyridine to provide 5-{[1,1-diphenyl-3-diisopropylamino]propyl}-2-methyl-1,3,4-oxadiazole, melting at 91°–92° C. The tetrazole intermediate has the following formula

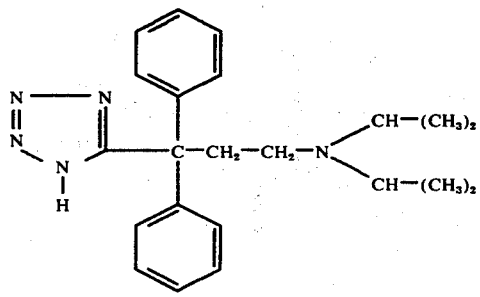

EXAMPLE 11

Following the procedures set out in Example 1, 16.8 parts of 2,2-diphenyl-3-methyl-4-dimethylaminovaleronitrile (U.S. Pat. No. 2,823,233), 5.3 parts of sodium azide, 4.3 parts of ammonium chloride, and 0.3 part of lithium chloride in 40 parts by volume of dimethylformamide are converted to 5-[1,1-diphenyl-3-dimethylamino]butyl-1H-tetrazole hydrochloride, melting at 281°–282° C. Also following the procedures of Example 1, 4.0 parts of the 1H-tetrazole free base and 4.9 parts of acetyl chloride in 40 parts by volume of pyridine are reacted to provide 5-{[1,1-diphenyl-3-dimethylamino]butyl}-2-methyl-1,3,4-oxadiazole hydrochloride, melting at 198°–204° C. The tetrazole intermediate has the following formula

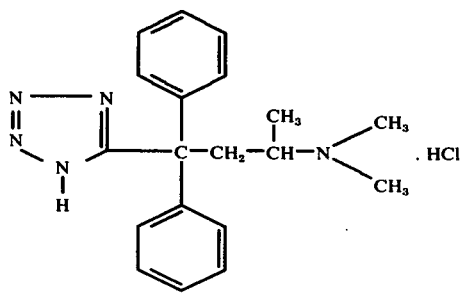

EXAMPLE 12

Following the procedures set out in Example 1, 26.6 parts of 2-phenyl-2-(2-pyridyl)-4-diisopropylaminobutyronitrile is reacted with 7.95 parts of ammonium chloride, 9.75 parts of sodium azide, and 0.15 part of lithium chloride in 75 parts by volume of dimethylformamide to provide 5-[1-phenyl-1-(2-pyridyl)-3-diisopropylamino]propyl-1H-tetrazole hydrochloride. Also following the procedure in Example 1, 1.1 parts of the above tetrazole is reacted with 1.15 parts of acetyl chloride in 10 parts by volume of pyridine to provide 5-{[1-phenyl-1-(2-pyridyl)-3-diisopropylamino]propyl}-2-methyl-1,3,4-oxadiazole, melting at 65°–67° C. The tetrazole intermediate has the following formula

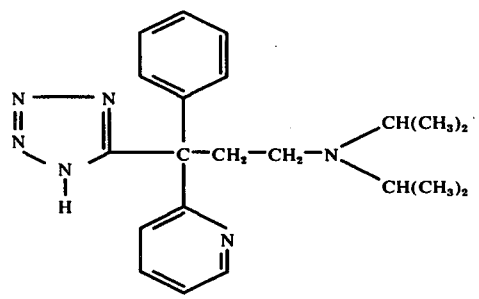

EXAMPLE 13

Following the procedures set out in Example 1, 26.6 parts of 2-phenyl-2-(p-chlorophenyl)-4-piperidinobutyronitrile (U.S. Pat. No. 2,823,233), is reacted with 7.95 parts of ammonium chloride, 9.75 parts of sodium azide and 0.15 part of lithium chloride in 75 parts by volume of dimethylformamide to provide 5-[1-phenyl-1-(p-chlorophenyl)-3-piperidino]propyl-1H-tetrazole hydrochloride. Also following the procedures in Example 1, 1.1 parts of the above tetrazole is reacted with 1.15 parts of acetyl chloride in 10 parts by volume of pyridine to provide 5-{[1-phenyl-1-(p-chlorophenyl)-3-piperidino]propyl}-2-methyl-1,3,4-oxadiazole. The tetrazole intermediate has the following formula

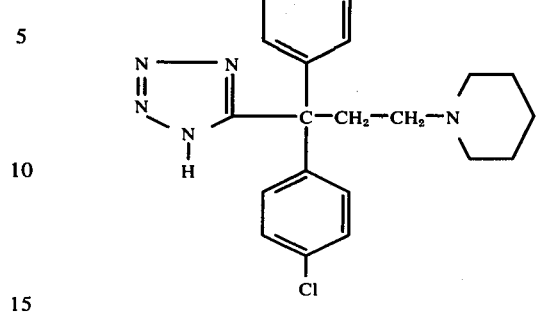

EXAMPLE 14

Following the procedures set out in Example 1, 26.6 parts of 4-diisopropylamino-2-(3-tolyl)-2-(2-pyridyl)-butyronitrile, described in U.S. Pat. No. 3,225,054, is reacted with 7.95 parts of ammonium chloride, 9.75 parts of sodium azide, and 0.15 part of lithium chloride in 75 parts by volume of dimethylformamide to provide 5-[1-(3-tolyl)-1-(2-pyridyl)-3-diisopropylamino]propyl-1H-tetrazole hydrochloride. Also following the procedures in Example 1, 1.1 parts of the above tetrazole is reacted with 1.15 parts of acetyl chloride in 10 parts by volume of pyridine to provide 5-{[1-(3-tolyl)-1-(2-pyridyl)-3-piperidino]propyl}-2-methyl-1,3,4-oxadiazole. The tetrazole intermediate has the following formula

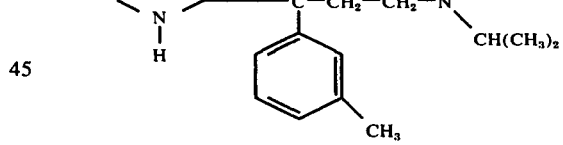

EXAMPLE 15

Following the procedures set out in Example 1, 26.6 parts of 2-(2-pyridyl)-2-(fluorophenyl)-4-diisopropyl-butyronitrile, U.S. Pat. No. 3,225,054, is reacted with 7.95 parts of ammonium chloride, 9.75 parts of sodium azide, and 0.15 part of lithium chloride in 75 parts by volume of dimethylformamide to provide 5-[1-(2-pyridyl)-1-(p-fluorophenyl)-3-diisopropylamino]propyl-1H-tetrazole hydrochloride. Also following the procedures in Example 1, 1.1 parts of the above tetrazole is reacted with 1.15 parts of acetyl chloride in 10 parts by volume of pyridine to provide 5-{[1-(2-pyridyl)-1-(p-fluorophenyl)-3-diisopropylamino]propyl}-2-methyl-1,3,4-oxadiazole. The tetrazole intermediate has the following formula

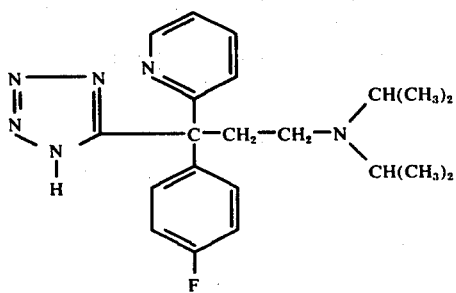

EXAMPLE 16

Using equivalent amounts and following the procedure in Example 3, 2-phenyl-2-(2-pyridyl)-4-(2-azabicyclo[2·2·2]oct-2-yl)butyronitrile is converted to 5-[1-phenyl-1-(2-pyridyl)-3-(2-azabicyclo[2·2·2]oct-2-yl)]propyl-1H-tetrazole, melting at 253°–254° C and this tetrazole is then converted to 5-{1-phenyl-1-(2-pyridyl)-3-(2-azabicyclo[2·2·2]oct-2-yl}-2-methyl-1,3,4-oxadiazole, melting at 109°–110° C. The tetrazole intermediate has the following formula

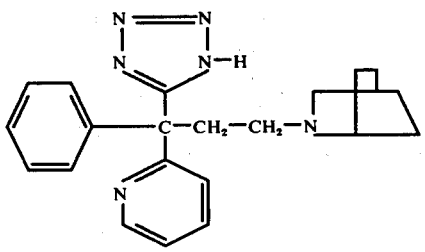

EXAMPLE 17

Following the procedure set out in Example 1, 2.6 parts of 5-[1,1-diphenyl-3-(2-azabicyclo[2·2·2]oct-2-yl)]propyl-1H-tetrazole are reacted with 2.0 parts by volume of trifluoroacetic acid anhydride in 20 parts by volume of pyridine to provide 5-{[1,1-diphenyl-3-(2-azabicyclo[2·2·2]oct-2-yl)]propyl}-2-trifluoromethyl-1,3,4-oxadiazole hydrochloride, melting at about 170° C.

EXAMPLE 18

Following the procedure set out in Example 1 1.85 parts of 5-[1,1-diphenyl-3-(2-azabicyclo[2·2·2]oct-2-yl)]propyl-1H-tetrazole are reacted with 3.4 parts of adamantane-1-carboxylic acid anhydride in 10 parts by volume of pyridine to provide 5-{[1,1-diphenyl-3-(2-azabicyclo[2·2·2]oct-2-yl)]propyl}-2-(1-tricyclo[3·3·1·1$^{3,7}$]decyl)-1,3,4-oxadiazole, melting at 127°–129.5° C.

EXAMPLE 19

Following the procedure set out in Example 1 3.7 parts of 5-[1,1-diphenyl-3-(2-azabicyclo[2·2·2]oct-2-yl)]propyl-1H-tetrazole are reacted with 2.3 parts by volume of benzoyl chloride in 10 parts by volume of pyridine to provide 5-{[1,1-diphenyl-3-(2-azabicyclo[2·2·2]oct-2-yl)]propyl}-2-phenyl-1,3,4-oxadiazole, melting at 140°–141° C.

EXAMPLE 20

Following the procedure of Example 19 and substituting an equivalent amount of p-methylbenzoyl chloride provides 5-{[1,1-diphenyl-3-(2-azabicyclo[2·2·2]oct-2-yl)]propyl)}-2-p-methylphenyl-1,3,4-oxadiazole.

EXAMPLE 21

Following the procedure of Example 19 and substituting an equivalent amount of p-chlorobenzoyl chloride provides 5-{[1,1-diphenyl-3-(2-azabicyclo[2·2·2]oct-2-yl)]propyl}-2-p-chlorophenyl-1,3,4-oxadiazole.

EXAMPLE 22

A mixture of 25 parts of benzyl cyanide, 35 parts of 3-bromopyridine and 220 parts of dry toluene is heated to 80° C with stirring. Then, 19 parts of sodamide is added portionwise over a period of 1 hour while the temperature is maintained at 80°–85° C with some cooling. The resultant mixture is heated to 105° C and a solution of 56 parts of 2-(2-chloroethyl)-2-azabicyclo[2·2·2]octane in 220 parts of dry toluene is added portionwise. The mixture is then heated at 105°–110° for an additional 3 hours before it is cooled and 250 parts of water are added. The organic layer is separated and dried and the solvent is evaporated to leave a residue which is dissolved in ether and filtered. The ether solvent is evaporated from the filtrate and the residual oil is distilled under reduced pressure to provide 2-phenyl-2-(3-pyridyl)-4-(2-azabicyclo[2·2·2]oct-2-yl)butyronitrile. Alternately α-phenyl-3-pyridylacetonitrile (U.S. Pat. No. 3,225,054) is reacted with 2-(2-chloroethyl)-2-azabicyclo[2·2·2]octane directly.

A mixture of 5.69 parts of 2-phenyl-2-(3-pyridyl)-4-(2-azabicyclo[2·2·2]oct-2-yl)butyronitrile, 1.67 parts of sodium azide, 1.38 parts of ammonium chloride and 0.025 parts of lithium chloride in 30 parts by volume of dimethylformamide was stirred for 12 hours under nitrogen at 120° C. After the reaction time was completed, the material was cooled and filtered. The collected precipitate is washed with dimethylformamide and water. The precipitate is then dissolved in 100 parts by volume of 0.2N NaOH. The resultant solution was filtered. The filtrates were neutralized with dilute hydrochloric acid. The product which separated was recrystallized from ethanol. The procedure afforded 5-[1-phenyl-1-(3-pyridyl)-3-(2-azabicyclo[2·2·2]oct-2-yl)]propyl-1H-tetrazole.

2.0 Parts of 5-[1-phenyl-1-(3-pyridyl)-3-(azabicyclo[2·2·2]oct-2-yl)]propyl-1H-tetrazole reacted with 4.0 parts of acetic anhydride in pyridine and refluxed for 2 hours to provide 5-[1-phenyl-1-(3-pyridyl)-3-(2-azabicyclo[2·2·2]oct-2-yl)]propyl-2-methyl-1,3,4-oxadiazole.

EXAMPLE 23

To a stirred suspension of 7 parts of sodamide in 90 parts of benzene maintained at 30°–35° C there is added a solution of α-phenyl-3-pyridylacetonitrile, described in U.S. Pat. No. 3,225,054, in 70 parts of benzene. The mixture is then refluxed for 1 hour, cooled and treated by portionwise addition with one equivalent of the propyl ester of 1-(2-chloroethyl)-4-phenylisonipecotic acid (U.S. Pat. No. 2,898,340 in 45 parts of xylene at 30°–40° C. The resulting mixture is refluxed for 2 hours, cooled, filtered and extracted with dilute hydrochloric acid. The The acid extract is rendered alkaline and extracted with ether. The ether extract is treated with gaseous hydrogen chloride to yield the hydrochloride of the propyl ester of 2-(3-pyridyl)-2-phenyl-4(4-carboxy-4-phenyl-1-piperidino)butyronitrile. Following the procedure set out in Example 1 and using equivalent quantities this butyronitrile is converted to 5-[1-phenyl-1-(3-pyridyl)-3-(4-carbpropoxy-4-phenylpiperidino)]propyl-1H-tetrazole which in turn is converted to 5-[1-phenyl-1-(3-pyridyl)-3-(4-carbpropoxy-4-phenylpiperidino)]propyl-2-methyl-1,3,4-oxadiazole. The structural formula of the tetrazole intermediate is

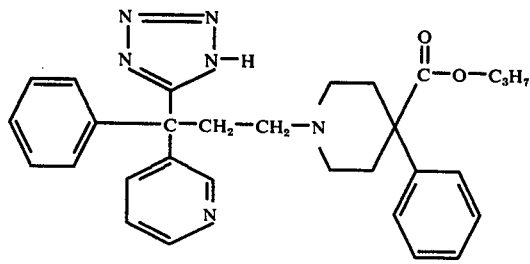

Hydrolysis of 1 part of 5-[1-phenyl-1-(3-pyridyl)-3-(4-carbopropoxy-4-phenylpiperidino)]propyl-1H-tetrazole with 15 parts of 20% aqueous sodium hydroxide and isolation provides 5-[1-phenyl-1-(3-pyridyl)-3-(4-carboxy-4-phenylpiperidino)]propyl-1H-tetrazole. Acid catalysed esterification in ethanol provides 5-[1-phenyl-1-(3-pyridyl)-3-(4-carbethoxy-4-phenyl-piperidino)]propyl-1H-tetrazole.

Treating 1 part of the acid with an excess of diborane in tetrahydrofuran at −10° C provides 5-[1-phenyl-1-(3-pyridyl)-3-(4-hydroxymethyl-4-phenylpiperidino)]-propyl-1H-tetrazole, having the following structural formula

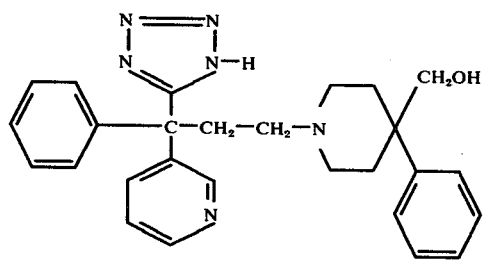

EXAMPLE 24

To a stirred suspension of 7 parts of sodamide in 90 parts of benzene maintained at 30°–35° C there is added a solution of α-phenyl-3-pyridylacetonitrile, described in U.S. Pat. No. 3,225,054 in 70 parts of benzene. The mixture is then refluxed for 1 hour, cooled and treated by portionwise addition with one equivalent of 2-morpholinoethyl chloride (J. Chem. Soc. pp 505, 1949) in 45 parts of xylene at 30°–40° C. The resulting mixture is refluxed for 2 hours, cooled, filtered and extracted with dilute hydrochloric acid. The acid extract is rendered alkaline and extracted with ether. The ether extract is treated with gaseous hydrogen chloride to yield the hydrochloride 2-phenyl-2-(3-pyridyl)-2-morpholinoethylbutyronitrile.

Following the procedure set out in Example 1 this nitrile is converted to 5-[1-phenyl-1-(3-pyridyl)-3-(morpholino)]propyl-1H-tetrazole which is converted to corresponding antidiarrheal oxadiazoles by methods described in previous examples.

What is claimed is:
1. A compound of the formula

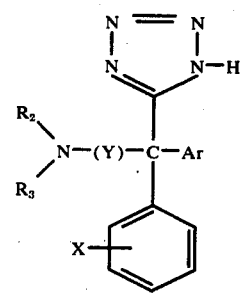

wherein Y is straight or branched chain alkylene having 1–4 carbon atoms; X is hydrogen, halo or lower alkyl containing 1–7 carbon atoms; Ar is pyridyl, phenyl, mono-substituted phenyl wherein the substituent is halo or lower alkyl having 1–7 carbon atoms; and $R_2$ and $R_3$ together with N is an azamonocyclic ring selected from the group comprising 1-pyrrolidinyl, piperidino, 4-phenyl-4-hydroxypiperidino, 4-phenyl-4-acetoxypiperidino, 4-phenyl-4-carboxypiperidino, 4-phenyl-4-carboloweralkoxypiperidino, or 4-phenyl-4-hydroxymethylpiperidino and morpholino.

2. A compound of the formula

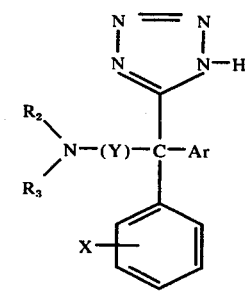

wherein Y is straight or branched chain alkylene containing 1–4 carbon atoms; X is hydrogen, halo, or lower alkyl having 1–7 carbon atoms; Ar is pyridyl, phenyl, monosubstituted phenyl wherein the substituent is halo or lower alkyl having 1–7 carbon atoms; and $R_2$ and $R_3$ together with N is an azabicycloalkanyl containing 6 to 9 carbon atoms and having at least 5 atoms in each ring of the azabicycloalkanyl.

3. A compound of the formula

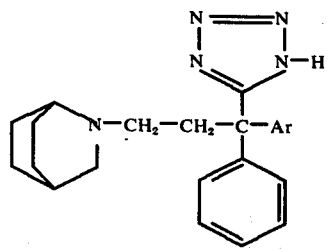

wherein Ar is phenyl or pyridyl.

4. A compound according to claim 3 which is 5-[1,1-diphenyl-3-(2-azabicyclo[2.2.2]oct-2-yl)]propyl-1H-tetrazole.

5. A compound according to claim 2 which is 5-[1,1-diphenyl-3-(3-azabicyclo[3.2.2]non-3-yl)]propyl-1H-tetrazole.

6. A compound according to claim 2 which is 5-[1-phenyl-1-(2-pyridyl)-3-(3-azabicyclo[3.2.2]non-3-yl)]propyl-1H-tetrazole.

7. A compound according to claim 2 which is 5-[1-phenyl-1-(2-pyridyl)-4-(3-azabicyclo[3.2.2]non-3-yl)]butyl-1H-tetrazole.

8. A compound according to claim 2 which is 5-[1,1-diphenyl-3-(8-azabicyclo[4.3.0]non-8-yl)]propyl-1H-tetrazole.

9. A compound according to claim 2 which is 5-[1,1-diphenyl-3-(6-azabicyclo[3.2.1]oct-6-yl)]propyl-1H-tetrazole.

10. A compound according to claim 2 which is 5-[1,1-diphenyl-3-(7-azabicyclo[2.2.1]hept-7-yl)]propyl-1H-tetrazole.

11. A compound according to claim 1 which is 5-[1,1-diphenyl-3-(4-hydroxy-4-phenylpiperidino)]propyl-1H-tetrazole.

12. A compound according to claim 1 which is 5-[1,1-diphenyl-3-(4-carbethoxy-4-phenylpiperidino)]propyl-1H-tetrazole.

13. A compound according to claim 1 which is 5-[1-phenyl-1-(2-pyridyl)-3-(2-azabicyclo[2.2.2]oct-2-yl)]propyl-1H-tetrazole.

14. A compound according to claim 3 which is 5-[1-phenyl-1-(3-pyridyl)-3-(2-azabicyclo[2.2.2]oct-2-yl)]propyl-1H-tetrazole.

15. A compound according to claim 1 which is 5-[1-phenyl-1-(3-pyridyl)-3-(4-hydroxymethyl-4-phenylpiperidino)]propyl-1H-tetrazole.

16. A compound according to claim 1 which is 5-[1-phenyl-1-(3-pyridyl)-3-(morpholino]propyl-1H-tetrazole.

* * * * *